(12) United States Patent
Cress

(10) Patent No.: US 7,309,329 B2
(45) Date of Patent: Dec. 18, 2007

(54) ASEPTIC EYEDROPPER WITH COLLECTING TROUGH AND CONVEX RELEASE SURFACE

(76) Inventor: Jonathan H. Cress, 526 Soquel Ave., Santa Cruz, CA (US) 95060

( * ) Notice: Subject to any disclaimer, the term of this patent is extended or adjusted under 35 U.S.C. 154(b) by 0 days.

(21) Appl. No.: 11/195,018

(22) Filed: Aug. 1, 2005

(65) Prior Publication Data

US 2005/0288640 A1    Dec. 29, 2005

Related U.S. Application Data (63) Continuation-in-part of application No. 11/099,322, filed on Apr. 4, 2005, which is a continuation-in-part of application No. PCT/US2004/027585, filed on Aug. 24, 2004, now abandoned, which is a continuation-in-part of application No. 10/648,138, filed on Aug. 25, 2003, now abandoned.

(51) Int. Cl.
*A61H 33/04* (2006.01)

(52) U.S. Cl. ............... 604/302; 604/294; 604/295; 604/296; 604/297; 604/298; 604/299; 604/300; 604/301

(58) Field of Classification Search ......... 604/294–302
See application file for complete search history.

(56) References Cited

U.S. PATENT DOCUMENTS

| | | | |
|---|---|---|---|
| 2,920,624 A * | 1/1960 | Lerner et al. ............ 604/301 |
| 3,446,209 A | 5/1969 | Macha | |
| 3,872,866 A * | 3/1975 | Lelicoff .................... 604/302 |
| 3,934,590 A * | 1/1976 | Campagna et al. ...... 604/302 |
| 4,085,750 A | 4/1978 | Bosshold | |
| 4,257,417 A | 3/1981 | Gibilisco | |
| 4,468,103 A | 8/1984 | Meckler | |
| 4,685,906 A | 8/1987 | Murphy | |
| 4,798,599 A | 1/1989 | Thomas | |
| 4,834,728 A * | 5/1989 | McKenna ................. 604/301 |
| 4,960,407 A | 10/1990 | Cope | |
| 4,973,322 A | 11/1990 | Jewart | |
| 5,059,188 A * | 10/1991 | Goddard ................... 604/300 |
| 5,171,306 A | 12/1992 | Vo | |
| 5,178,613 A | 1/1993 | Gibilisco | |
| 5,320,615 A * | 6/1994 | Van Keuren .............. 604/297 |
| D369,211 S | 4/1996 | Weiler | |
| 5,665,079 A | 9/1997 | Stahl | |
| 5,713,495 A | 2/1998 | Menard | |
| 5,836,927 A * | 11/1998 | Fried ....................... 604/300 |
| 6,319,240 B1 | 11/2001 | Beck | |
| 6,325,784 B1 | 12/2001 | Muroff | |
| D457,952 S | 5/2002 | Sherman | |
| D463,550 S | 9/2002 | Sherman | |
| 6,595,970 B1* | 7/2003 | Davidian .................. 604/300 |
| 6,736,802 B1 | 5/2004 | Recanati | |
| 2002/0016576 A1 | 2/2002 | Lee | |

* cited by examiner

*Primary Examiner*—Tatyana Zalukaeva
*Assistant Examiner*—Ginger T. Chapman
(74) *Attorney, Agent, or Firm*—Townsend and Townsend and Crew LLP (57) ABSTRACT

Apparatus for attaching to a squeeze bottle or other dispenser for delivering drops to an eye comprises an axial member and a laterally extending leg. The axial member is attached to the bottle and receives drops or liquid therefrom. The leg is rested against the patient's nose bridge so that it directs fluid to a trough and releases drops into the eye after a predetermined threshold volume is exceeded.

6 Claims, 10 Drawing Sheets

ASEPTIC EYEDROPPER WITH COLLECTING TROUGH AND CONVEX RELEASE SURFACE

CROSS-REFERENCES TO RELATED APPLICATIONS

This application is a continuation-in-part of U.S. application Ser. No. 11/099,322, filed on Apr. 4, 2005, now abandoned which was a continuation-in-part of PCT/US04/27585, filed on Aug. 24, 2004, which was a continuation-in-part of U.S. application Ser. No. 10/648,138, filed on Aug. 25, 2003, now abandoned the full disclosures of which are incorporated herein by reference.

BACKGROUND OF THE INVENTION

1. Field of the Invention

The present invention relates generally to medical apparatus and methods. More particularly, the present invention relates to eyedropper construction and methods for using eyedroppers to deliver drops to the inner corner of a patient's eye.

Many if not most people find dispensing eye drops into their own eyes to be an uncomfortable procedure. Many people blink or shake as the drops are released from the conventional eyedropper, often leading to incomplete delivery of the irrigant lubricant or medication.

Despite many attempts to provide improved systems, the most common technique for self-dispensation of eye drops remains use of a dropper bottle. The patient turns his or her eyes upwardly, locates a dispensing nozzle of the dropper over the eye, and squeezes the bottle to dispense the drop. Sometimes this works. Sometimes this doesn't work.

Prior attempts at improving eyedroppers and systems are almost too numerous to mention. Of particular interest to the present invention, a variety of eye drop dispensing guides or positioners have been developed. For the most part, these improved guides or dispensers have been attempts to stabilize and/or position the dispensing nozzle of the dropper or dropper bottle at some predetermined position over the eye. In some cases, the guides or positioners have further included means for holding the eyelid open in an attempt to assure that the drop actually enters the eye.

While potentially being helpful, the location of the dropper or dropper bottle over the eye still can be disturbing or even daunting to the patient. Moreover, most of these guides or positioners have been threatening, somewhat uncomfortable, cumbersome, unaesthetic, and awkward to use.

For these reasons, it would be desirable to provide additional and improved devices and apparatus for accurately and successfully dispensing drops into a patient's eyes. In particular, it would be desirable if the apparatus and systems were easy to use, did not require placement of the dispensing bottle or dropper directly over an eye, and could provide accurate and reproducible delivery of a drop to a particular area of the eye, more particularly the inner corner (medial canthus) of the eye. At least some of these objectives will be met by the invention as described and claimed hereinbelow.

2. Description of the Background Art

Patents describing eyedroppers and other devices for directing drops into eyes include U.S. Pat. Nos. 6,595,970; 6,325,784; 6,319,240; 5,713,495; 5,665,079; 5,059,188; 4,973,322; 4,960,407; 4,685,906; 4,468,103; 4,257,417; 4,085,750; and 3,934,590. See also published application US 2002/0016576 and design patents D463,550; D457,952; and D369,211. The full disclosures of each of these patents and applications are incorporated herein by reference.

BRIEF SUMMARY OF THE INVENTION

The present invention provides drop dispensing apparatus and methods intended particularly for delivering drops to an eye from a generally conventional drop applicator, such as a squeeze bottle. In particular, the apparatus comprises a drop dispensing attachment which is adapted to receive drops from such a squeeze bottle and to direct the drops into a patient's eye, particularly to the inner corner of the eye, i.e., the medial canthus. The drop dispensing attachment may be provided as a separate component which is capable of being attached to an otherwise conventional drop dispensing squeeze bottle. Alternatively, the attachment may be formed as an integral part of such a squeeze bottle or other dispenser and/or may include a special connector which allows the attachment to be removably attached to squeeze bottles or other dispensers having a special mating attachment.

Droplet dispensing attachments according to the present invention comprise an axial member having an inlet which receives drops from the squeeze bottle and a cross member attached to the axial member. The cross member includes a nose bridge rest which is adapted to rest on the patient's nose bridge. In exemplary embodiments, the nose bridge rest is axially aligned with the axial member and the attached squeeze bottle so that the patient is able to hold the squeeze bottle and advance the nose rest over the patient's own nose bridge so that the bottle is between the eyes, not directly over either eye.

The cross member of the dispensing attachment further includes at least one leg extending laterally relative to the axial member (usually the nose bridge rest as well). The laterally extending leg has an outlet which is connected to receive drops from the inlet in the axial member. The outlet is further adapted and positioned so that it will release drops from the outlet into the patient's eye when the rest is positioned over the patient's nose bridge. In the preferred and exemplary embodiments, the outlet will be positioned so that the drop is released into the inner corner of the eye. In this way, there is little or no structure which is positioned directly over the patient's eye, significantly reducing the negative perception which many patients feel when placing an eyedropper over their eye.

It is particularly desirable that the drop be dispensed into the eye with little or no residual drop remaining on the dispensing attachment. The elimination of residual volume helps assure that the drops will have a consistent and repeatable volume. The elimination of residual also reduces the chance of contaminating the dispensing device. Such elimination of residual fluid on the dispensing device and accurate and repeatable dispensing volumes can be achieved by providing a trough or other holding structure on the dispensing attachment. The trough will be disposed to receive fluid from the squeeze bottle as it is laterally channeled in the first leg. In particular, the trough will usually be defined on a laterally outward surface of the first leg and have a retaining wall which collects fluid as the bottle is squeezed and the attachment held in its vertically aligned position on the patient's nose bridge. The fluid will build up in the trough until it reaches a threshold volume, typically in the range from 10 µl to 60 µl, preferably 20 µl to 40 µl. After the threshold volume is reached or exceeded, a droplet will form that will flow over the trough, then over a convex surface and into the patient's eye. The droplet will preferably pass from the trough onto a laterally outward surface of the first leg, where the surface is preferably hydrophobic so that the drop will flow immediately off the surface and into the eye.

DETAILED DESCRIPTION OF THE INVENTION

Figure 1:
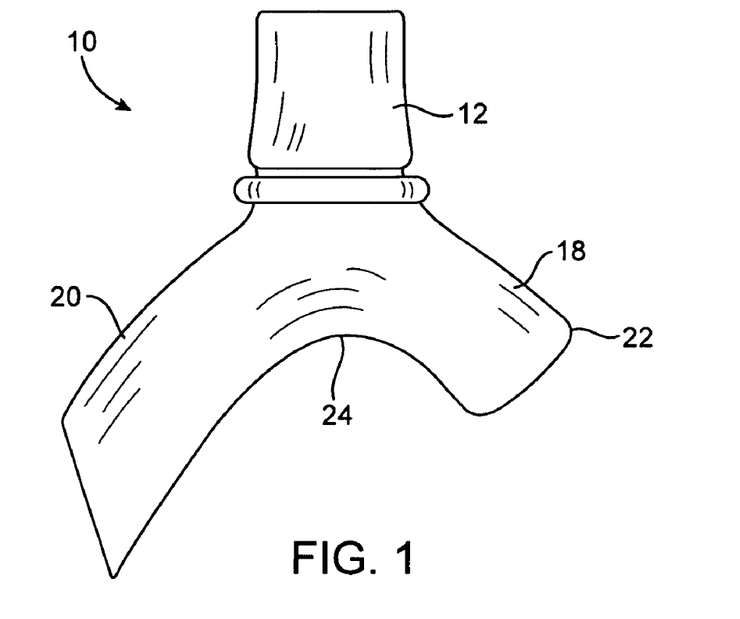
FIG. 1 is a side view of a drop dispensing attachment constructed in accordance with the principles of the present invention.
Figure 2:
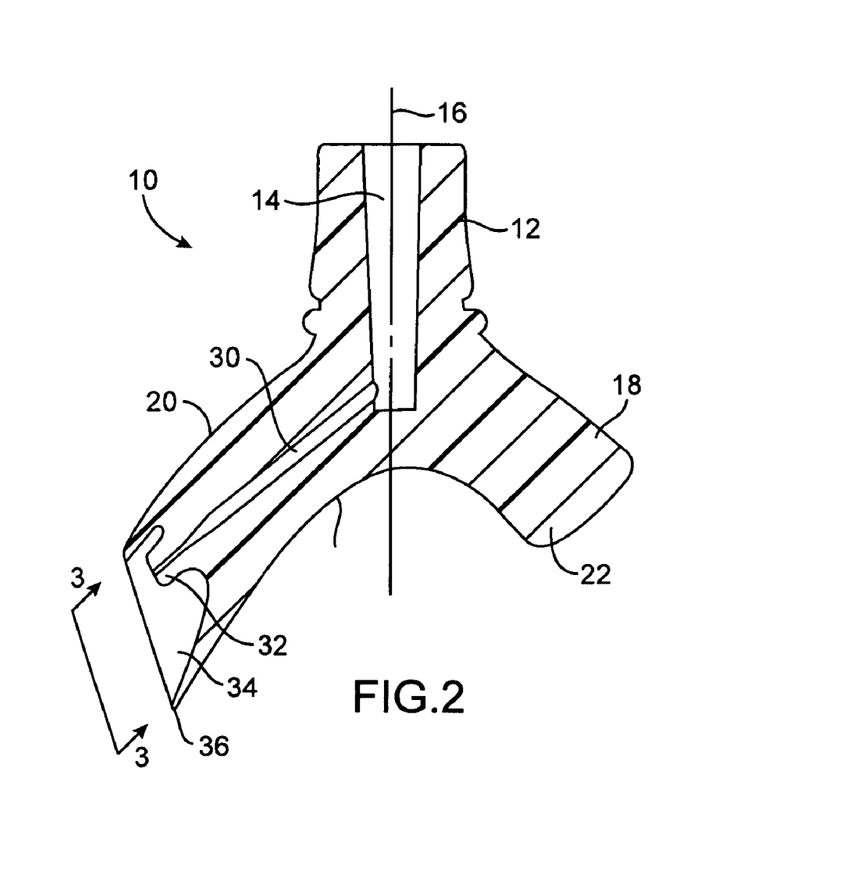
FIG. 2 is a cross-sectional view of the drop dispensing attachment of FIG. 1.
Figure 3:
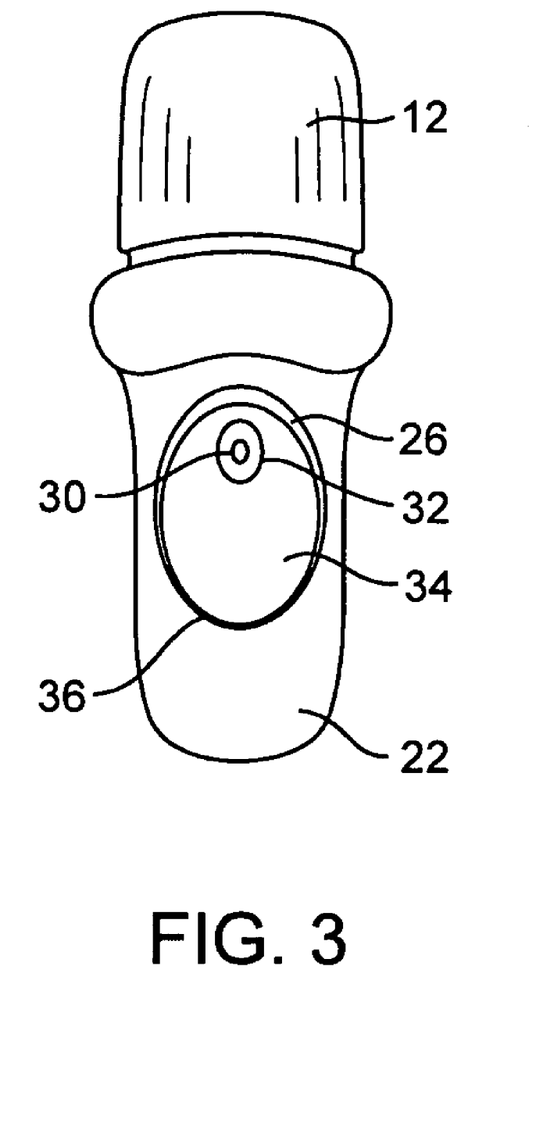
FIG. 3 is an end view of a laterally extending leg of a cross-member of the drop dispensing apparatus of FIGS. 1 and 2 taken along line 3-3 of FIG. 2.

An exemplary drop dispensing attachment 10 constructed in accordance with the principles of the present invention is illustrated in FIGS. 1-3. The attachment 10 includes an axial member 12 having an inlet lumen 14 aligned generally along a longitudinal axis 16 of the device. A cross member 18 is attached to the axial member 12 and includes at least one laterally extending leg 20 and usually a second laterally extending leg 22. Preferably, the legs 20 and 22 are arranged in an arcuate geometry to define a nose bridge rest region 24 therebetween. The laterally extending leg 20 includes an outlet lumen 30 which preferably terminates in a nozzle 32 found within a recess 34 in the end of the leg 20. Preferably, the recess 34 terminates in a very thin circumferential segment or "lip" 36 at its lower end which will be positioned at the medial canthus or inner corner of the eye during the dispensing procedure, as described in more detail below. The thin lip 36 is desirable since it puts the drop in contact with the skin, thereby drawing it away from the device by capillary action and reducing the possibility of back contamination of the device and the bottle's content.

The axial member 12 will be adapted to be removably (or in some cases permanently) attached to a squeeze bottle or other droplet dispenser. Although not illustrated in detail, the axial member may be threaded, provided with an interference fit, or otherwise specially adapted to removably receive the squeeze bottle. Alternatively, of course, the attachment 10 could be formed as an integral part of the squeeze bottle or other droplet dispenser.

The attachment 10 may be formed from a variety of materials, typically being cast or molded from a suitable polymer typically polyethylene, or silicone, typically having a Shore A hardness from 30 to 55. The dimensions are chosen to fit a typical patient, with the lumens having diameters from 0.25 mm to 1 mm, the nozzle diameter being from 0.25 mm to 1 mm, and the distance from the axis 16 to the lip 36 being 15 mm to 25 mm. The materials are preferably malleable and conform to a variety of nasal bridge contours.

Figure 4:
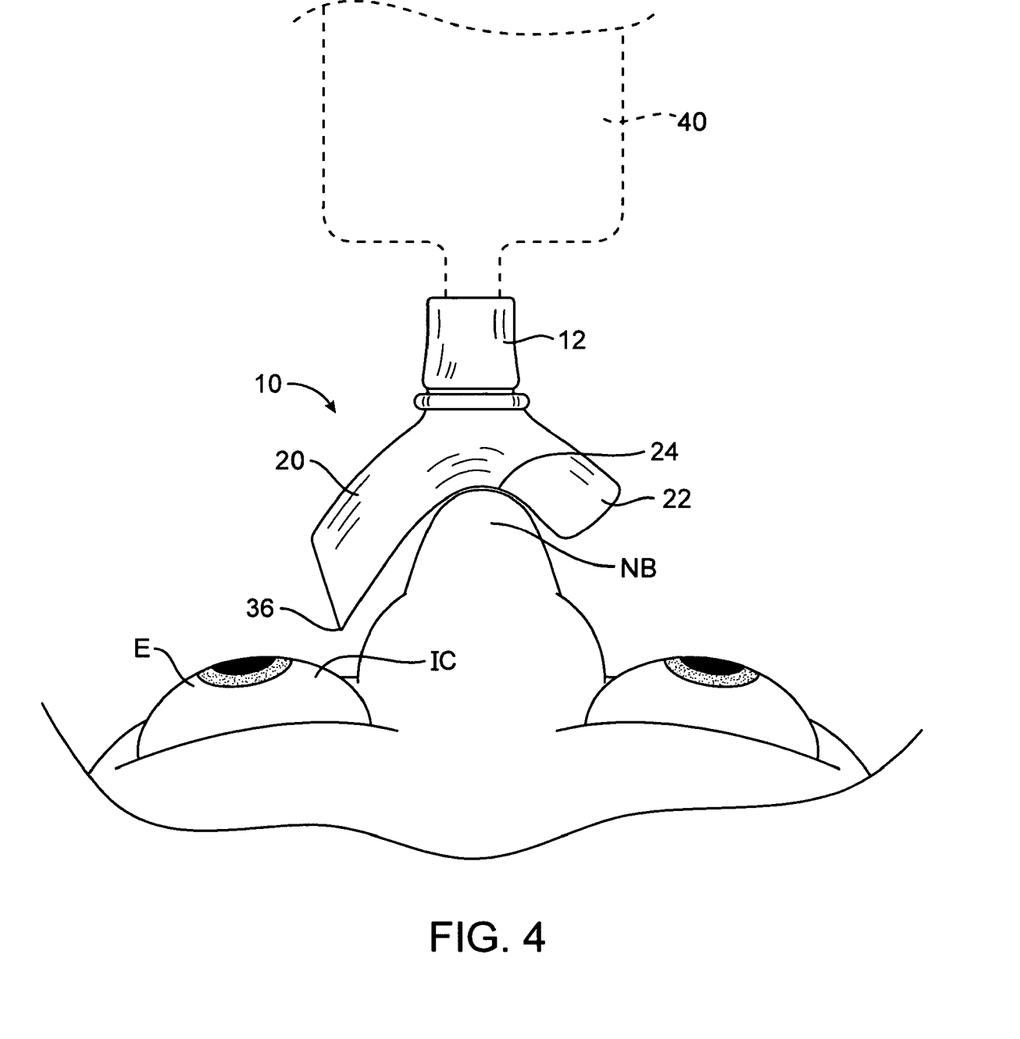
FIGS. 4 and 5 illustrate use of the apparatus of FIGS. 1-3 for dispensing drops into an inner corner of a patient's eye.
Figure 5:
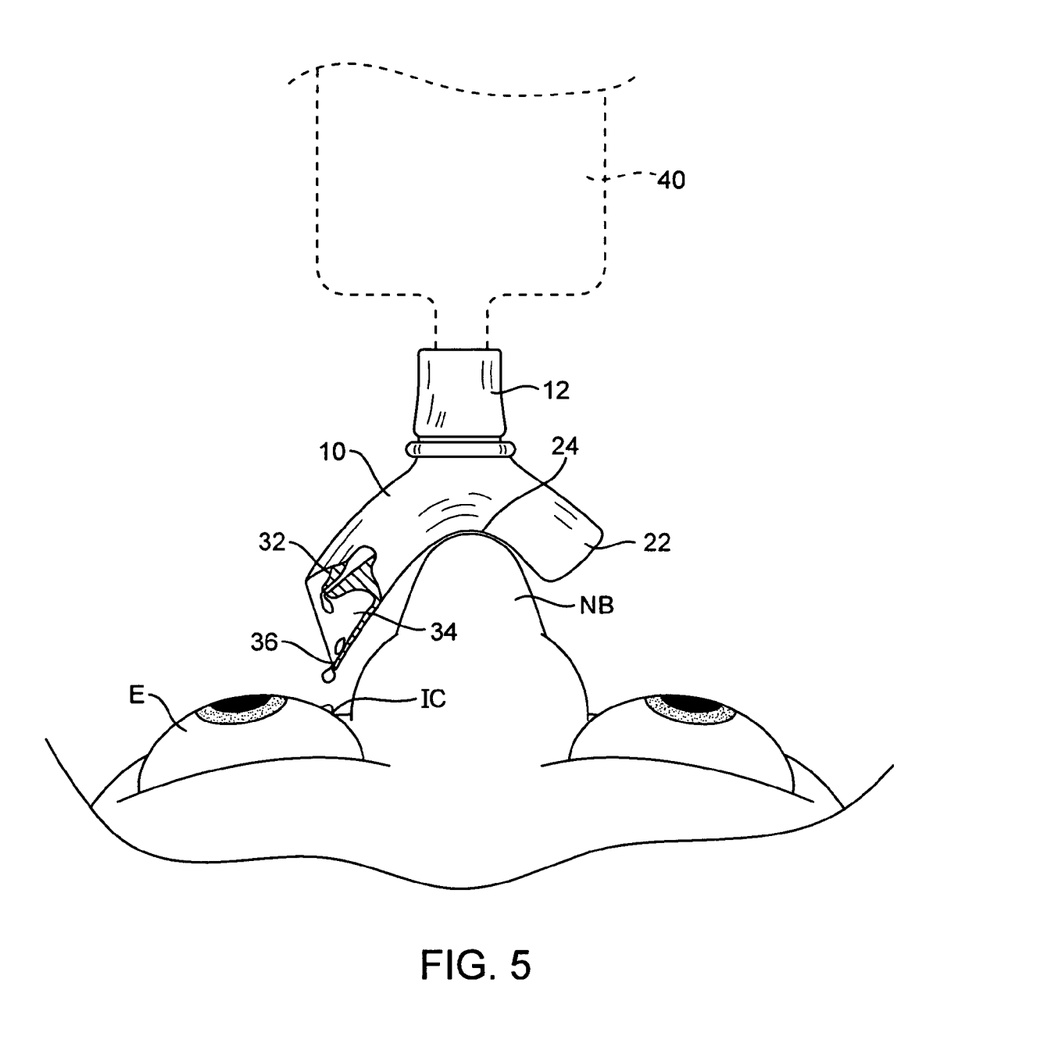

Referring now to FIGS. 4 and 5, use of the attachment 10 attached to a dispensing bottle 40 for delivering drops to an eye E of a patient will be described. Initially, the patient attaches the attachment 10 to the bottle 40, if it has not already been done. After that, the patient may hold the bottle, or in some cases less desirably the attachment 10, in order to 25 engage the nose bridge region 24 of the attachment against the nose bridge NB of the patient. The assembly of the attachment 10 and squeeze bottle 40 will be held so that the lip 36 of the leg 20 is positioned over the inner corner IC of the eye E. Proper positioning of the assembly will generally be as shown in FIG. 4, where the assembly is generally between the eyes rather than over either eye.

By squeezing the bottle 40, droplets are dispensed through the attachment 10 and out of the nozzle 32, as illustrated in FIG. 5. The droplets will fall onto the inner wall of the recess 34 and then from the lip 36 and slide into the eye.

Conveniently, if the patient wishes to dispense drops into the other eye, the assembly of the bottle 40 and attachment 10 may simply be turned 180° about the axis 16 so that the dispensing leg 20 now lies over the other eye. The bottle may then be squeezed to deliver lubricant, medication, and/or irrigant to the other eye as just described with respect to the first eye.

Figure 6:
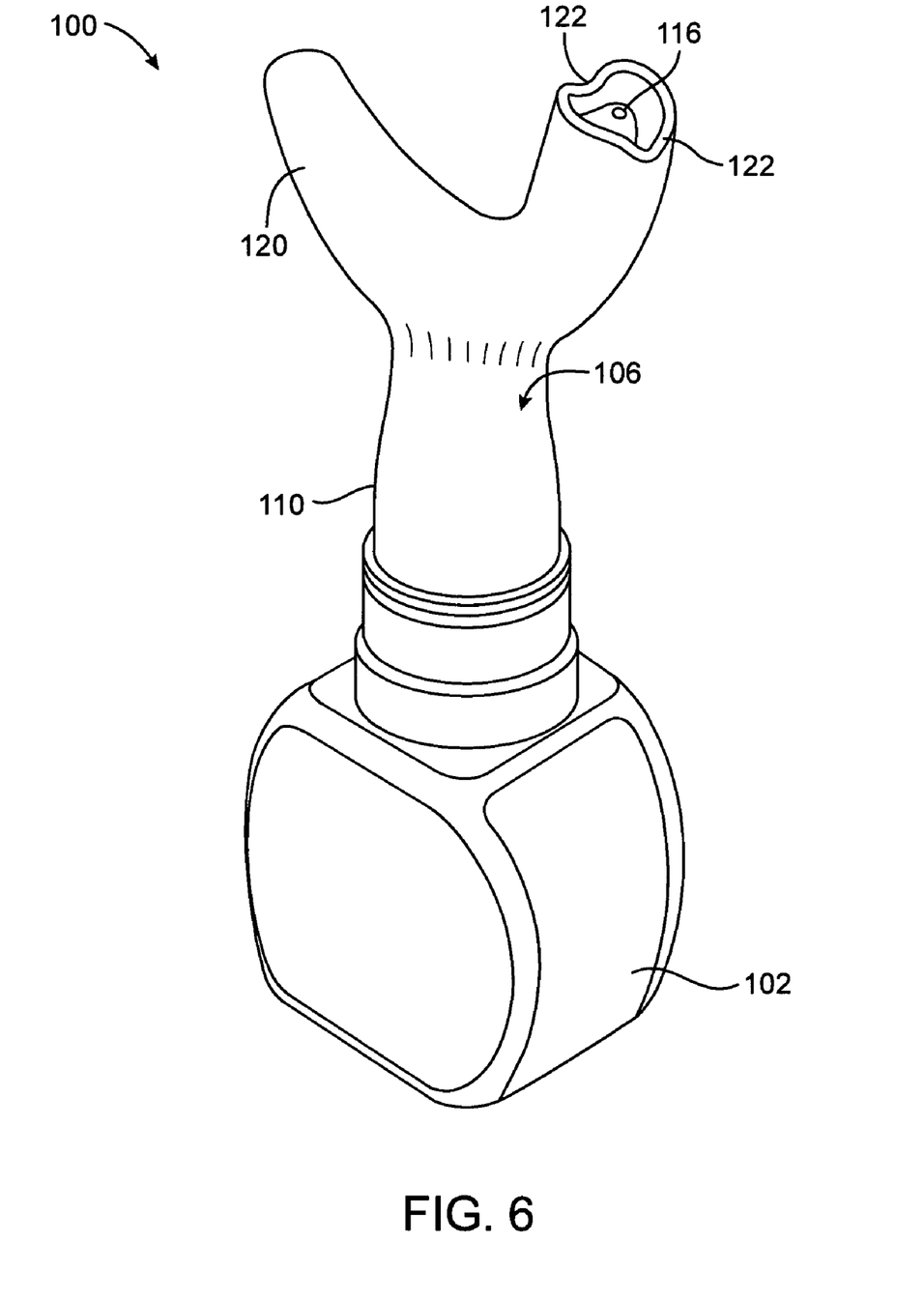
FIG. 6 is a perspective view of an alternative drop dispensing system constructed in accordance with the principles of the present invention.
Figure 7:
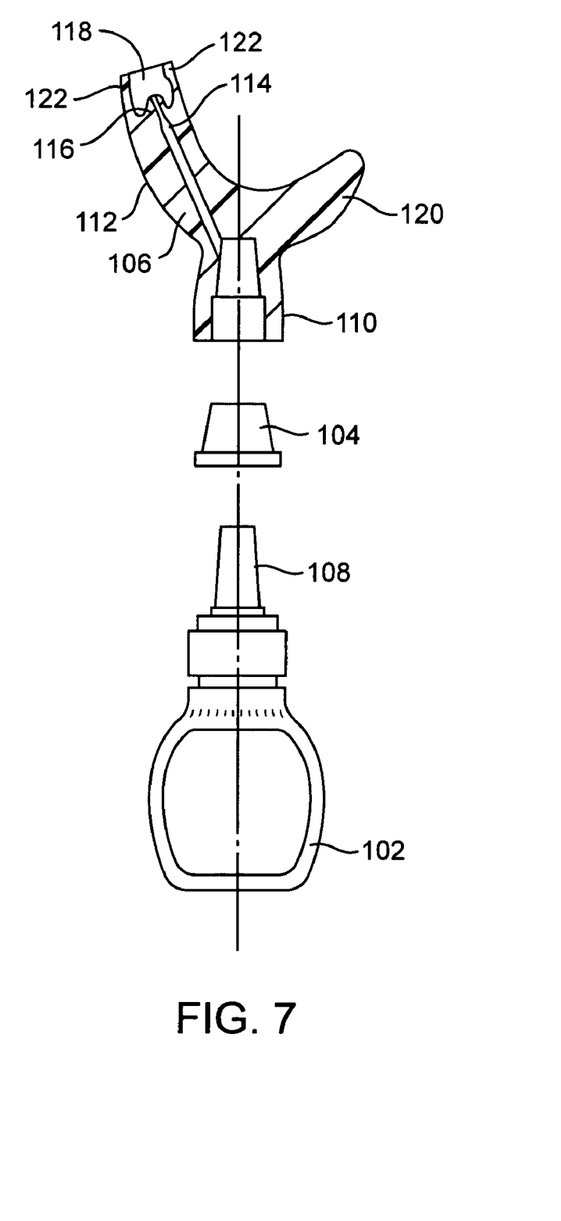
FIG. 7 is an exploded view of the system of FIG. 6, shown with the attachment in cross-section.
Figure 8:
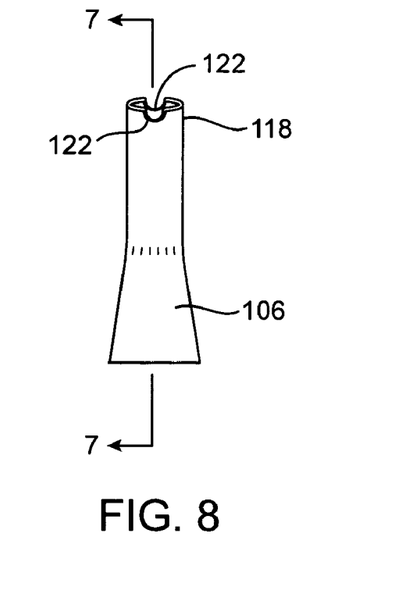
FIG. 8 is a side-view of the attachment showing a cross-sectional line 7-7.

A drop dispensing system 100 constructed in accordance with the principles of the present invention and comprising a dropper bottle 102, a compression ring 104, and an attachment 106 for laterally deflecting the eye drop is illustrated in FIGS. 6-8. The dropper bottle 102 can be any conventional eye dropper having a tip 108 intended to dispense a drop in a conventional manner. The attachment 106 is a modified version of the attachments described earlier, as will be described in more detail below. The compression ring 104 is adapted to permit removable placement of the attachment 106 on the tip 108. Thus, it will be appreciated that an axial member 10 and the compression ring 104 can be modified and constructed as appropriate to allow removable attachment to any type of eye dropper bottle available to be modified. The materials and general dimensions of the attachment 106 may be similar or identical to those described earlier for attachment 10. The principal differences between attachment 106 and the prior attachment 110 is that the laterally extending leg 112 which carries the outlet lumen 114 and nozzle 116 extends over a greater arc length than that of the prior embodiment. As will be described in more detail with respect to FIG. 9 below, this modified configuration allows the nozzle 116 to dispense a drop directly into the eye without the drop first landing on any portion of the peripheral wall of recess 118. The attachment 106 will typically comprise a second leg 120 to complete the cross-member.

The attachment 106 further differentiates the earlier attachment in that a pair of cut-outs 122 are formed in the peripheral wall about recess 118, as best seen in FIG. 8. These cut-outs help assure that the drop will not contact the peripheral wall and further provide venting of the recessed region when the device is in use dispensing a drop into the eye.

Figure 9:
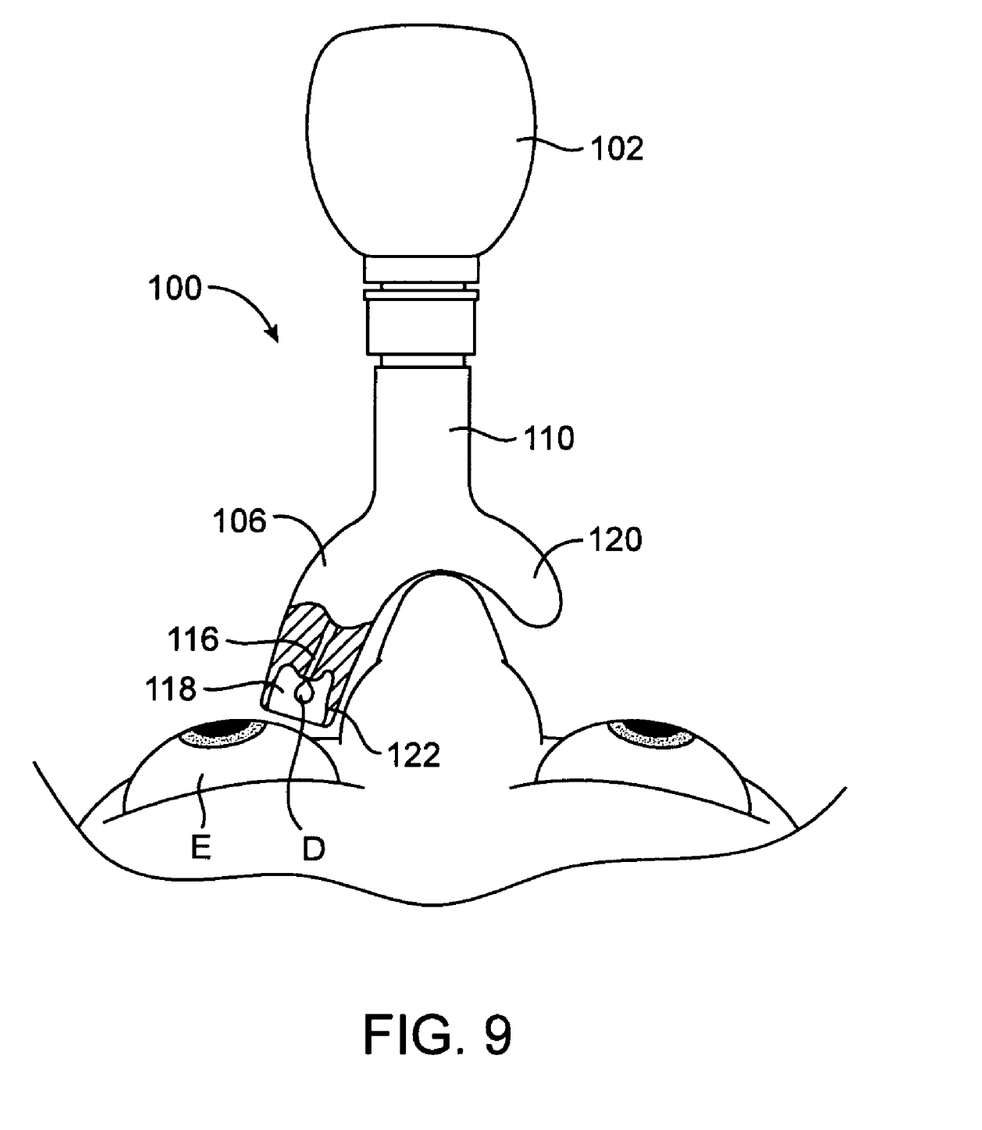
FIG. 9 illustrates use of the device of FIG. 6 for dispensing a drop directly into an eye.

Referring now to FIG. 9, the dropper bottle system 100 is used by placing the middle of the cross-member against the patient's nose bridge so that the lateral arm 116 is generally over the inner corner of the patient's eye E. The axis of axial member 110 will be held vertically and the nozzle 116 will be able to dispense a drop D directly into the corner of the eye, while the cut-out and remaining peripheral wall around the recess 118 contacts the inner portion of the eye or tissue surrounding the eye. Cut-out 122 helps prevent pooling of the droplet and helps vent the region within the recess, although presence of the cut-out is not essential for proper operation of the device.

Figure 10:
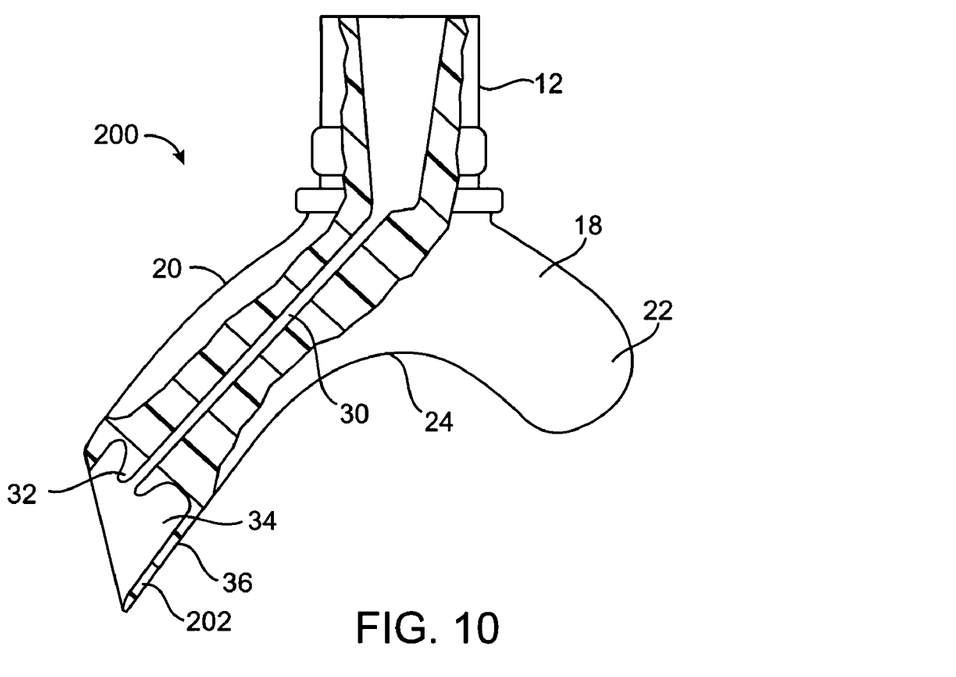
FIGS. 10 and 11 illustrate a further alternative structure for a nozzle arrangement according to the present invention.

FIG. 10 illustrates an attachment 200 which has a geometry very similar to that of attachment 10 (FIGS. 1 and 2), except that a large cut-out 202 is formed in the lower lip 36 of the attachment. All other numbering in FIG. 10 will be the same as in FIGS. 1 and 2.

Figure 11:
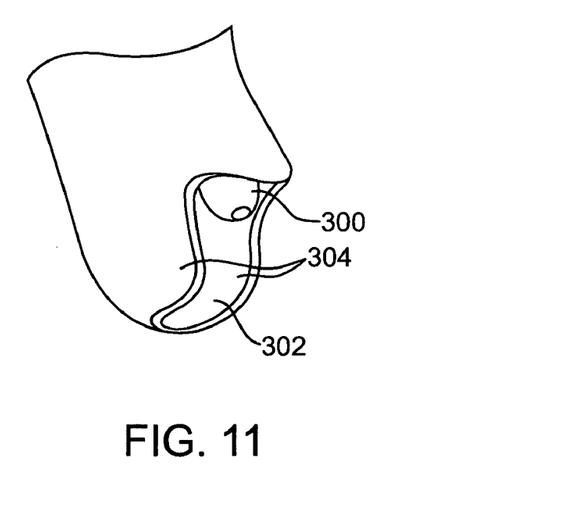
Figure 12A:
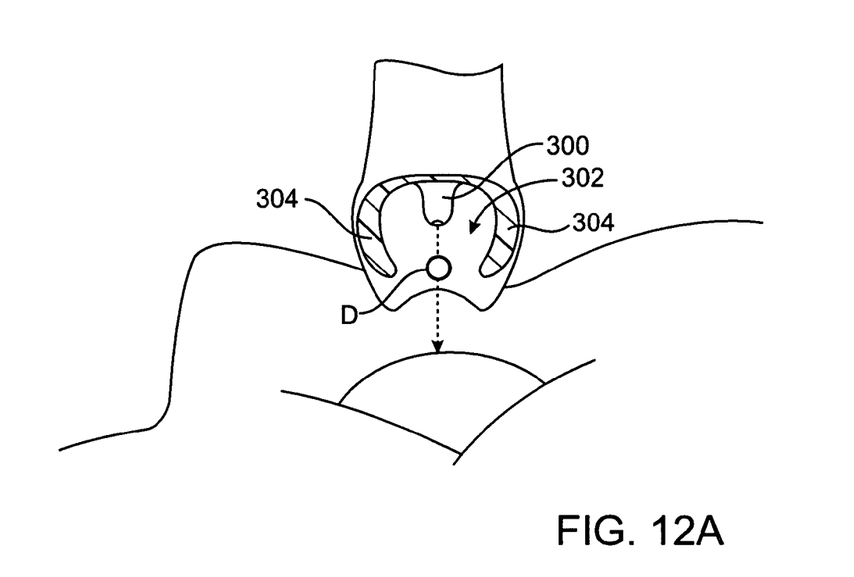
FIGS. 12A and 12B illustrate use of the device of FIGS. 9 and 10 for dispensing drops at different head inclinations.
Figure 12B:
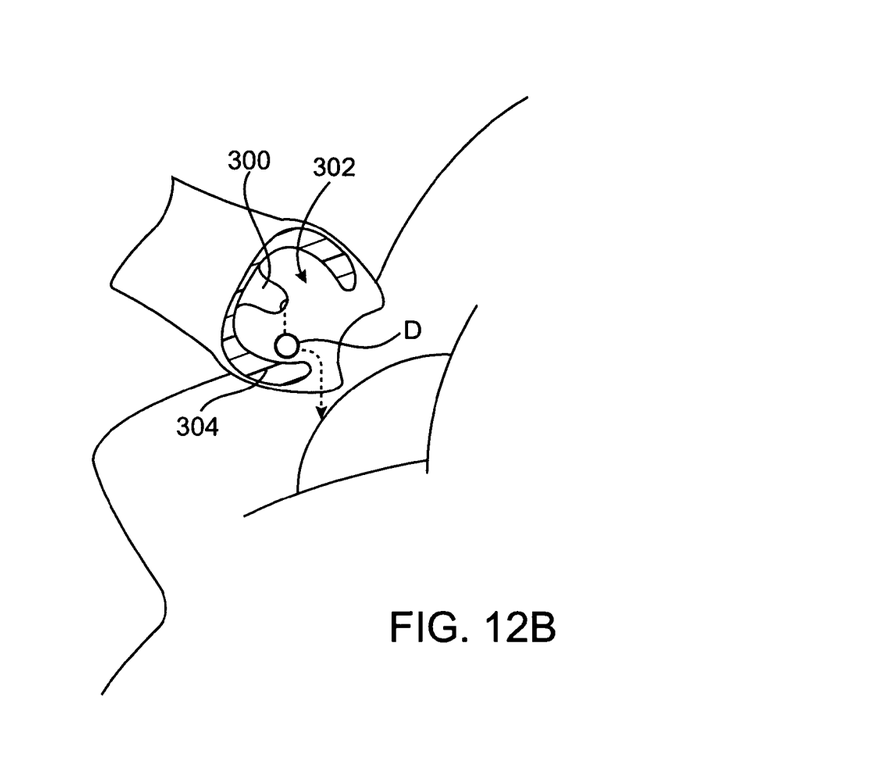

A still further embodiment of a nozzle 300 oriented vertically over an opening or aperture 302 in a cross-member 318 is illustrated in FIG. 11. The opening 302 of the nozzle 300 is defined by inwardly flared walls 304. The nozzle 300 will release a drop D directly over the eye with little risk of contacting an edge of the cross-member, thus significantly reducing any opportunity for contamination of the device or bottle contents, as illustrated in FIG. 12A where the patient has fully tilted his or her head. The inwardly flared side walls 304 will act to redirect the drop D to the medial canthal or inner corner of the eye even when the head is not inclined fully back, as illustrated in FIG. 12B.

Figure 13:
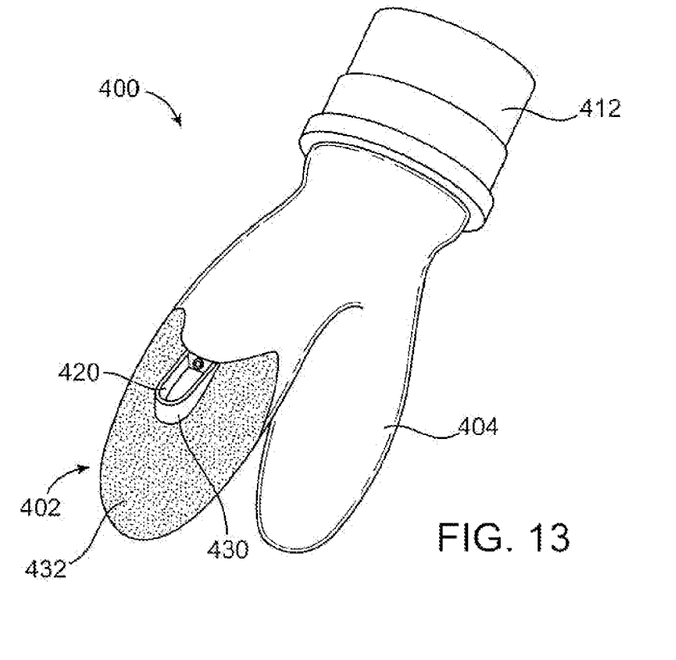
FIG. 13 is a perspective view of a further alternative drop dispensing attachment constructed in accordance with the principles of the present invention.
Figures 14, 14A:
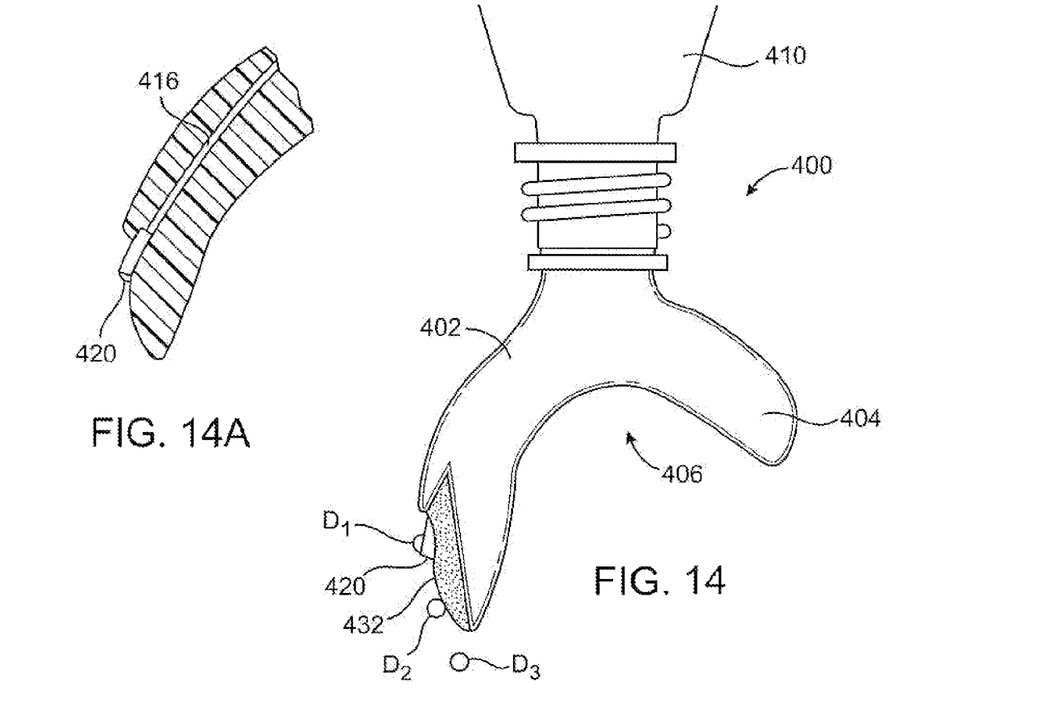
FIG. 14 is a side-view of the attachment of FIG. 13, showing the drop release mechanism.
FIG. 14A is a detailed, cross-sectional view of a first leg of the attachment of FIGS. 13 and 14 showing the fluid delivery channel and fluid collecting trough of the attachment.

In yet another embodiment of the present invention as shown in FIGS. 12, 14A and 14B, a drop dispensing attachment 400 comprises a first leg 402 and second leg 404 having a region 406 therebetween configured to rest on the patient's nose bridge, as described previously. A squeeze bottle (FIG. 14) receives an inlet 412 of the attachment 400 so that squeezing the bottle delivers fluid through a channel 416 (FIG. 14A) which releases a drop through a port 417 to a trough 420. The drop is protected by an overhang 418 which reduces the risk of the port 417 becoming contaminated. The fluid from channel 416 will build up in the trough 420 until a threshold volume is exceeded, allowing a droplet $D_1$ to form, flow over a distal lip 430 of the trough having isolated the drop from the port 417, and then flow down over convex surface 432 as shown at $D_2$, until the drop is released, as shown at $D_3$. The surface 432 is preferably treated to be hydrophobic, e.g. by plasma etching or other conventional treatment.

While the invention has been described with reference to specific embodiments, the description is illustrative of the invention and is not to be construed as limiting the invention. Various modifications and applications may occur to those skilled in the art without departing from the true spirit and scope of the invention as defined by the appended claims.

What is claimed is:

1. A drop dispensing attachment adapted to receive drops of fluid from a squeeze bottle and to direct drops to an eye of a patient having a nose bridge, said attachment comprising:
    an axial member having a threaded inlet end adapted to attach to a squeeze bottle and an inlet lumen which receives fluid from the squeeze bottle; and
    a cross member attached to an opposite end of the squeeze bottle and having a channel and a first leg extending laterally from the axial member, wherein the cross-member includes a trough and a separate convex surface, wherein the channel receives fluid from the inlet lumen and directs the fluid through the channel to the trough, wherein the trough collects a threshold volume of fluid and after the volume has been collected releases the volume as a drop onto the convex surface which directs the drop into the eye when the cross member is positioned over the nose bridge.

2. An attachment as in claim 1, wherein the cross member includes a second leg and has an arcuate shape with two symmetric legs, further composing a nose bridge rest is disposed between the legs.

3. An attachment as in claim 2, wherein the first laterally extending leg is shorter than the second leg.

4. An attachment as in claim 1, wherein the convex surfure is hydrophobic.

5. An attachment as in claim 1, wherein the trough comprises a barrier retaining wall which surrounds an outlet of a channel in the first leg.

6. A system for dispensing droplets, said system comprising:
    an attachment as in claim 1; and
    a squeeze bottle attached to deliver drops to the attachment.

* * * * *